(12) United States Patent
Michal et al.

(10) Patent No.: US 8,257,722 B2
(45) Date of Patent: *Sep. 4, 2012

(54) LOCAL DELIVERY OF WATER-SOLUBLE OR WATER-INSOLUBLE THERAPEUTIC AGENTS TO THE SURFACE OF BODY LUMENS

(75) Inventors: Eugene T. Michal, San Francisco, CA (US); Daniel J. Lerner, Scarsdale, NY (US); Matthew J. Pollman, San Francisco, CA (US)

(73) Assignee: CV Ingenuity Corp., Atherton, CA (US)

( * ) Notice: Subject to any disclaimer, the term of this patent is extended or adjusted under 35 U.S.C. 154(b) by 369 days.

This patent is subject to a terminal disclaimer.

(21) Appl. No.: 12/210,344

(22) Filed: Sep. 15, 2008

(65) Prior Publication Data

US 2010/0069879 A1 Mar. 18, 2010

(51) Int. Cl.
*A61F 13/00* (2006.01)
(52) U.S. Cl. ..................................... 424/422
(58) Field of Classification Search ............. None
See application file for complete search history.

(56) References Cited

U.S. PATENT DOCUMENTS

| | | | |
|---|---|---|---|
| 4,010,259 A | 3/1977 | Johansson | |
| 4,589,873 A | 5/1986 | Schwartz et al. | |
| 4,847,324 A | 7/1989 | Creasy | |
| 4,950,256 A | 8/1990 | Luther et al. | |
| 5,001,009 A | 3/1991 | Whitbourne | |
| 5,256,701 A | 10/1993 | Tamura et al. | |
| 5,302,392 A * | 4/1994 | Karakelle et al. | 424/409 |
| 5,302,394 A | 4/1994 | Beahm | |
| 5,304,121 A | 4/1994 | Sahatjian | |
| 5,331,027 A | 7/1994 | Whitbourne | |
| 5,464,650 A | 11/1995 | Berg et al. | |
| 5,525,348 A | 6/1996 | Whitbourne et al. | |
| 5,616,608 A | 4/1997 | Kinsella et al. | |
| 5,662,609 A | 9/1997 | Slepian | |
| 5,674,192 A | 10/1997 | Sahatjian et al. | |
| 5,733,888 A | 3/1998 | Carver et al. | |
| 5,733,925 A | 3/1998 | Kunz et al. | |
| 5,762,638 A | 6/1998 | Shikani et al. | |
| 5,788,979 A | 8/1998 | Alt et al. | |
| 5,811,447 A | 9/1998 | Kunz et al. | |
| 5,886,026 A | 3/1999 | Hunter et al. | |
| 5,900,246 A | 5/1999 | Lambert | |
| 5,954,706 A | 9/1999 | Sahatjian | |
| 5,972,992 A | 10/1999 | Carver et al. | |
| 5,977,164 A | 11/1999 | Carver et al. | |
| 6,074,659 A | 6/2000 | Kunz et al. | |
| 6,096,070 A | 8/2000 | Ragheb et al. | |
| 6,096,331 A | 8/2000 | Desai et al. | |
| 6,110,483 A | 8/2000 | Whitbourne et al. | |
| 6,120,784 A * | 9/2000 | Snyder, Jr. | 424/404 |
| 6,146,358 A | 11/2000 | Rowe | |
| 6,218,016 B1 | 4/2001 | Tedeschi et al. | |
| 6,268,390 B1 | 7/2001 | Kunz | |
| 6,299,604 B1 | 10/2001 | Ragheb et al. | |
| 6,306,166 B1 | 10/2001 | Barry et al. | |
| 6,306,421 B1 | 10/2001 | Kunz et al. | |
| 6,369,039 B1 | 4/2002 | Palasis et al. | |
| 6,403,635 B1 | 6/2002 | Kinsella et al. | |
| 6,419,692 B1 | 7/2002 | Yang et al. | |
| 6,429,232 B1 | 8/2002 | Kinsella et al. | |
| 6,506,411 B2 | 1/2003 | Hunter et al. | |
| 6,515,009 B1 | 2/2003 | Kunz et al. | |
| 6,537,579 B1 | 3/2003 | Desai et al. | |
| 6,544,544 B2 | 4/2003 | Hunter et al. | |
| 6,638,767 B2 | 10/2003 | Unger et al. | |
| 6,638,797 B2 * | 10/2003 | Noguchi et al. | 438/149 |
| 6,663,881 B2 | 12/2003 | Kunz et al. | |
| 6,673,053 B2 | 1/2004 | Wang et al. | |
| 6,730,064 B2 | 5/2004 | Ragheb et al. | |
| 6,753,071 B1 | 6/2004 | Pacetti | |
| 6,774,278 B1 | 8/2004 | Ragheb et al. | |
| 6,835,387 B2 | 12/2004 | Herrmann | |
| 6,846,815 B2 | 1/2005 | Myers et al. | |
| 6,855,770 B2 | 2/2005 | Pinchuk et al. | |
| 6,918,927 B2 | 7/2005 | Bates et al. | |
| 6,926,919 B1 | 8/2005 | Hossainy et al. | |

(Continued)

FOREIGN PATENT DOCUMENTS

EP 0681475 8/1994

(Continued)

OTHER PUBLICATIONS

PCT International Search Report and Written Opinion for International Application No. PCT/US2009/056842, mailed Dec. 17, 2009, 8 pages. PCT International Search Report and Written Opinion for International Application No. PCT/US2009/056842, mailed Mar. 31, 2010, 17 pages.
Katsuda, S., et al., "The Role of Cytoplasmic Microtubules in Regulation of Smooth Muscle Proliferation." International Atherosclerosis Society Poster Sessions, Abstract Book from 8th International Symposium on Atherosclerosis, Rome, Oct. 9-13, 1988, p. 446.
U.S. Appl. No. 12/121,692, filed May 15, 2008, Kerrigan, Cameron K.
PCT International Preliminary Report on Patentability for International Application No. PCT/US2009/056842, issued Mar. 15, 2011, 7 pages.
PCT International Search Report and Written Opinion for International Application No. PCT/US2010/027731, mailed Mar. 21, 2011, 11 pages.
Jones, David S., Poly($\epsilon$-caprolactone) and poly($\epsilon$-caprolactone)-polyvinylpyrrolidone-iodine blends as ureteral biomaterials: characterisation of mechanical and surface properties, degration and resistance to encrustation in vitro., Biomaterials, vol. 23, pp. 4449-4458, 2002.
Weaver, J.V.M., et al., "Stimulus-Responsive Water-Soluble Polymers Based on 2-Hydroxyethyl Methacrylate"Macromolecules, vol. 37 (7), pp. 2395-2403, Mar. 2004.

(Continued)

*Primary Examiner* — Bethany Barham
(74) *Attorney, Agent, or Firm* — Blakely Sokolof Taylor & Zafman LLP

(57) ABSTRACT

A method and device for local delivery of water-soluble or water-insoluble therapeutic agents to the surface of a normal or diseased body lumen is disclosed. An expandable structure of a medical disposable device, such as a balloon of a balloon catheter, is coated with an amphiphilic polymer coating comprising a therapeutic agent and an amphiphilic polymer or co-polymer. The medical disposable device is inserted into a body lumen, and expanded to contact the amphiphilic polymer coating against the body lumen. The total solubility of the polymer or co-polymer in vivo prevents any embolic hazard associated with the amphiphilic polymer coating.

21 Claims, 3 Drawing Sheets

U.S. PATENT DOCUMENTS

| | | |
|---|---|---|
| 7,008,979 B2 | 3/2006 | Schottman et al. |
| 7,105,175 B2 | 9/2006 | Schwarz |
| 7,179,251 B2 | 2/2007 | Palasis |
| 7,279,174 B2 | 10/2007 | Pacetti et al. |
| 7,291,165 B2 | 11/2007 | Rosenthal et al. |
| 7,381,418 B2 | 6/2008 | Richard |
| 7,407,507 B2 | 8/2008 | Maeda et al. |
| 7,482,034 B2 | 1/2009 | Boulais |
| 7,541,047 B2 | 6/2009 | Rogasch et al. |
| 2002/0151844 A1 | 10/2002 | Yang et al. |
| 2003/0052424 A1 | 3/2003 | Turner et al. |
| 2003/0059454 A1 | 3/2003 | Barry et al. |
| 2003/0203991 A1 | 10/2003 | Schottman et al. |
| 2003/0225451 A1 | 12/2003 | Sundar |
| 2004/0017007 A1 | 1/2004 | Chiu et al. |
| 2004/0073284 A1 | 4/2004 | Bates et al. |
| 2004/0117006 A1 | 6/2004 | Lewis et al. |
| 2004/0175406 A1 | 9/2004 | Schwarz |
| 2004/0241094 A1 | 12/2004 | Chung et al. |
| 2005/0004661 A1 | 1/2005 | Lewis et al. |
| 2005/0036946 A1* | 2/2005 | Pathak et al. .................. 424/9.4 |
| 2005/0059965 A1 | 3/2005 | Eberl et al. |
| 2005/0147690 A1* | 7/2005 | Masters et al. ................ 424/499 |
| 2005/0159704 A1 | 7/2005 | Scott et al. |
| 2005/0226903 A1 | 10/2005 | Rogasch et al. |
| 2005/0250672 A9 | 11/2005 | Speck et al. |
| 2005/0278021 A1 | 12/2005 | Bates et al. |
| 2006/0020243 A1 | 1/2006 | Speck et al. |
| 2006/0020331 A1 | 1/2006 | Bates et al. |
| 2006/0034769 A1 | 2/2006 | Kohn et al. |
| 2006/0212106 A1 | 9/2006 | Weber et al. |
| 2006/0228453 A1 | 10/2006 | Cromack et al. |
| 2006/0240070 A1 | 10/2006 | Cromack et al. |
| 2007/0065481 A1 | 3/2007 | Chudzik et al. |
| 2007/0065482 A1 | 3/2007 | Chudzik et al. |
| 2007/0065483 A1 | 3/2007 | Chudzik et al. |
| 2007/0065484 A1 | 3/2007 | Chudzik et al. |
| 2007/0071792 A1 | 3/2007 | Varner et al. |
| 2007/0104766 A1* | 5/2007 | Wang et al. ................... 424/443 |
| 2007/0190103 A1 | 8/2007 | Hossainy et al. |
| 2008/0020013 A1 | 1/2008 | Reyes et al. |
| 2008/0021385 A1 | 1/2008 | Barry et al. |
| 2008/0078400 A1 | 4/2008 | Martens et al. |
| 2008/0102033 A1 | 5/2008 | Speck et al. |
| 2008/0102034 A1 | 5/2008 | Speck et al. |
| 2008/0113035 A1 | 5/2008 | Hunter |
| 2008/0118543 A1 | 5/2008 | Pacetti et al. |
| 2008/0118544 A1 | 5/2008 | Wang |
| 2008/0124372 A1 | 5/2008 | Hossainy et al. |
| 2008/0132992 A1 | 6/2008 | Bates et al. |
| 2008/0140002 A1 | 6/2008 | Ramzipoor et al. |
| 2008/0145396 A1 | 6/2008 | Bates et al. |
| 2008/0146489 A1 | 6/2008 | Pacetti et al. |
| 2008/0153900 A1 | 6/2008 | Hunter |
| 2008/0175887 A1 | 7/2008 | Wang |
| 2008/0311173 A1 | 12/2008 | Schwarz et al. |
| 2009/0054837 A1 | 2/2009 | Von Holst et al. |
| 2009/0074707 A1 | 3/2009 | Rogasch et al. |
| 2009/0098176 A1 | 4/2009 | Helmus et al. |
| 2009/0112239 A1 | 4/2009 | To |
| 2009/0136560 A1 | 5/2009 | Bates et al. |
| 2009/0186414 A1 | 7/2009 | Srivastava et al. |
| 2009/0196931 A1 | 8/2009 | Kunz et al. |
| 2009/0216317 A1 | 8/2009 | Cromack et al. |
| 2009/0218731 A1 | 9/2009 | Rogasch et al. |
| 2009/0227948 A1 | 9/2009 | Chen et al. |
| 2009/0227949 A1 | 9/2009 | Knapp et al. |
| 2009/0285974 A1 | 11/2009 | Kerrigan |
| 2009/0297584 A1 | 12/2009 | Lim et al. |
| 2010/0015200 A1 | 1/2010 | McClain et al. |
| 2010/0030183 A1 | 2/2010 | Toner et al. |
| 2010/0063570 A1 | 3/2010 | Pacetti et al. |
| 2010/0137975 A1 | 6/2010 | Wittchow |
| 2011/0070355 A1 | 3/2011 | Bavaro et al. |

FOREIGN PATENT DOCUMENTS

| | | |
|---|---|---|
| EP | 0706376 B1 | 6/1997 |
| EP | 1011743 | 2/1999 |
| EP | 1011171 | 6/2000 |
| EP | 1539267 | 4/2004 |
| EP | 1632259 | 3/2006 |
| EP | 1649853 | 4/2006 |
| EP | 1666092 B1 | 6/2006 |
| EP | 1372737 B8 | 12/2006 |
| EP | 0706376 B2 | 8/2007 |
| EP | 1666071 B1 | 8/2007 |
| EP | 1986711 | 8/2007 |
| EP | 1666070 B1 | 9/2007 |
| EP | 2004251 | 10/2007 |
| EP | 2010244 | 10/2007 |
| EP | 1857127 | 11/2007 |
| EP | 1539266 B1 | 4/2008 |
| EP | 0797988 B1 | 1/2009 |
| EP | 2200674 A2 | 3/2009 |
| EP | 1118325 B2 | 1/2010 |
| EP | 1669092 | 3/2010 |
| EP | 1669092 A1 | 3/2010 |
| EP | 2193813 | 6/2010 |
| WO | WO 91/12779 | 9/1991 |
| WO | WO 93/11120 | 6/1993 |
| WO | WO 94/16706 | 8/1994 |
| WO | WO 95/03036 | 2/1995 |
| WO | WO 98/58988 | 12/1998 |
| WO | WO 9908729 | 2/1999 |
| WO | WO 01/28589 | 4/2001 |
| WO | WO 2004028610 | 4/2004 |
| WO | WO 2006/022754 | 3/2006 |
| WO | WO 2007/035865 | 3/2007 |
| WO | WO 2007094940 | 8/2007 |
| WO | WO 2007/111885 | 10/2007 |
| WO | WO 2007112006 | 10/2007 |
| WO | WO 2009036014 | 3/2009 |
| WO | WO 2009/124570 | 10/2009 |
| WO | WO 2010/030995 A2 | 3/2010 |

OTHER PUBLICATIONS

CV Ingenuity Office Action for U.S. Appl. No. 12/210,344 mailed Jun. 24, 2011.

CV Ingenuity Office Action for U.S. Appl. No. 12/712,134 mailed Mar. 31, 2011.

CV Ingenuity Office Action for U.S. Appl. No. 12/726,101 mailed Mar. 30, 2011.

B. Braun Vascular Systems, "SeQuent® Please", Product Brochure No. 6050120, accessed Sep. 9, 2009 at http://www.deb-bbraun.com/doc/doc_download.cfm?6736&uuid=9E5F74B02A5AE6266471CF5AF5F43933&&IRACER_AUTOLINK&&, B. Braun Melsungen AG Vascular Systems, 10 pages, Berlin, Germany.

B. Braun Vascular Systems, "SeQuent® Please", Product Brochure No. 6050120, http://www.deb-bbraun.com/doc/doc_download.cfm?6736&uuid=9E5F74B02A5AE6266471CF5AF5F43933&&IRACER_AUTOLINK&&, B. Braun Melsungen AG Vascular Systems, 10 pages, Berlin, Germany, Feb. 2008.

Consigny, P. Macke et al., "Local Delivery of an Antiproliferative Drug with Use of Hydrogel-coated Angioplasty Balloons!", Journal of Vascular and Interventional Radiology, vol. 5, No. 4, pp. 554-560, Jul.-Aug. 1994.

CV Ingenuity Notice of Allowance for U.S. Appl. No. 12/712,134 mailed Oct. 3, 2011.

CV Ingenuity Notice of Allowance for U.S. Appl. No. 12/726,101 mailed Sep. 29, 2011.

CV Ingenuity Office Action for U.S. Appl. No. 12/210,344 mailed Nov. 7, 2011.

Gray, William A., et al., "Drug-Coated Balloons for the Prevention of Vascular Restenosis" Circulation: Journal of the American Heart Association, vol. 121, pp. 2672-2680, accessible at http://circ.ahajournals.org/cgi/content/full/121/24/2672, American Heart Association, Dallas, TX, 2010.

* cited by examiner

LOCAL DELIVERY OF WATER-SOLUBLE OR WATER-INSOLUBLE THERAPEUTIC AGENTS TO THE SURFACE OF BODY LUMENS

BACKGROUND

1. Field

Embodiments of the present invention relate to the field of medical therapeutic agent delivery. More particularly embodiments of this invention relate to methods and devices used for local delivery of water-soluble or water-insoluble therapeutic agents to the surface of normal or diseased body lumens.

2. Background Information

Sporadic, inherited, environmental, and iatrogenic diseases associated with significant morbidity and mortality develop in the wall of endothelial cell-lined and epithelial cell-lined body lumens. For example, atherosclerosis and post-procedural restenosis develop in the arterial wall. Adenocarcinoma, esophageal varices, and cholangiocarcinoma develop in the gastrointestinal tract wall. The efficacy of systemic drug therapy for these diseases may be limited by inadequate drug delivery to the diseased tissue and/or dose limiting toxic effects in non-diseased tissue. Local delivery of drugs to diseased tissue in body lumen walls can overcome these limitations: therapeutic concentrations of drugs can be achieved without systemic toxicity.

SUMMARY

Embodiments of the present invention disclose a novel approach to coating an expandable structure of a medical disposable device, such as a balloon of a balloon catheter, which can be used for local therapeutic agent delivery to the surface of body lumens. The approach permits forming a coating with high levels of a therapeutic agent (e.g. paclitaxel) and utilizes a unique chemical formulation designed to permit forming a coating that provides a uniform therapeutic agent density across the balloon surface using a simple, reproducible and hence easily manufacturable application process. This novel coating process can be used to locally delivery a uniform dose of water-soluble and water-insoluble therapeutic agents to treat a variety of diseases that arise in body lumen walls. In addition, the novel coating approach may accommodate therapeutic levels of combinations of therapeutic agents (e.g. paclitaxel and dexamethasone acetate) directed at distinct therapeutic targets to increase the therapeutic efficiency of the procedure.

In an embodiment, a coating solution is single-dip coated on an expandable structure having an outer surface, such as an angioplasty balloon useful for either coronary or peripheral arteries, in order to form an amphiphilic polymer coating on the outer surface of the expandable structure. The coating solution contains an amphiphilic polymer or co-polymer in majority or exclusively non-aqueous solvents, a therapeutic agent or combination of therapeutic agents (e.g. paclitaxel and dexamethasone acetate), and an optional plasticizer and/or wax. In an embodiment, the amphiphilic polymer or co-polymer is complexed with iodine, which is not covalently bound to the amphiphilic polymer or co-polymer. The coating solution may also contain a plurality of amphiphilic polymers or co-polymers. After coating, the balloon is dried and folded for delivery.

The coated medical disposable device may then be used in a therapeutic operation. In an embodiment, the coated medical disposable device is inserted into a body lumen and expanded to contact the amphiphilic polymer coating against the body lumen. Hydration of the coating occurs immediately when exposed to aqueous fluids, such as blood in vivo, causing the amphiphilic polymer coating to dissolve and the therapeutic agent to release into tissue of the body lumen. The total solubility of the polymer or co-polymer in blood prevents any embolic hazard associated with the amphiphilic polymer coating. In an embodiment, at least 90% of the amphiphilic polymer coating is dissolved within 300 seconds of inflating, and more preferably with 90 seconds of inflating. Also, this active dissolution of the polymer or co-polymer matrix assists the transfer of hydrophobic therapeutic agents such as paclitaxel from the balloon to the tissue.

DETAILED DESCRIPTION

Figure 1A:
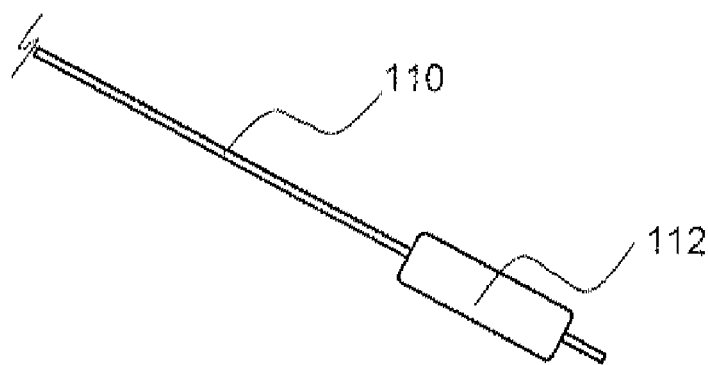
FIG. 1A is a side view illustration of a balloon catheter while the balloon is in the expanded position.

Embodiments of the present invention disclose methods and devices used for local delivery of water-soluble or water-insoluble therapeutic agents to the surface of normal or diseased body lumens.

Various embodiments described herein are described with reference to figures. However, certain embodiments may be practiced without one or more of these specific details, or in combination with other known methods and configurations. In the following description, numerous specific details are set forth, such as specific configurations, compositions, and processes, etc., in order to provide a thorough understanding of the present invention. In other instances, well-known processes and manufacturing techniques have not been described in particular detail in order to not unnecessarily obscure the present invention. Reference throughout this specification to "one embodiment" or "an embodiment" means that a particular feature, configuration, composition, or characteristic described in connection with the embodiment is included in at least one embodiment of the invention. Thus, the appearances of the phrase "in one embodiment" or "an embodiment" in various places throughout this specification are not necessarily referring to the same embodiment of the invention. Furthermore, the particular features, configurations, compositions, or characteristics may be combined in any suitable manner in one or more embodiments.

In one aspect, embodiments of the invention disclose a medical disposable device in which an amphiphilic polymer coating is disposed on the outer surface of an expandable structure. The amphiphilic polymer coating includes at least one therapeutic agent and at least one amphiphilic polymer or co-polymer. The amphiphilic polymer coating may optionally include additional components such as a plasticizer and/or wax. The therapeutic agent can be either water-soluble or water-insoluble. Hydration of the amphiphilic polymer coating occurs immediately when exposed to aqueous fluids such as blood in vivo causing the amphiphilic polymer coating to dissolve and the therapeutic agent to release into tissue of the body lumen. The total solubility of the polymer or co-polymer in blood prevents any embolic hazard associated with the amphiphilic polymer coating.

In an embodiment, the medical disposable device is a catheter with an expandable balloon having an amphiphilic polymer coating comprising a therapeutic agent. The catheter is advanced within a body lumen to align the balloon with the target tissue, the balloon is expanded to 2-20 atmospheres to bring the amphiphilic polymer coating into contact with the target tissue, causing the amphiphilic polymer coating to dissolve and the therapeutic agent payload to release rapidly to the target tissue in vivo because the device will contact the target tissue for only a short amount of time, approximately 5 to 300 seconds. Because the device is to be used for only a short time period and then removed from the body, it is considered to be a "medical disposable" device rather than "implantable."

The term amphiphilic as used herein means dissolvable in aqueous solvents such as, but not limited to, blood in-vivo, as well as in non-aqueous solvents such as, but not limited to, ethanol, methanol, and/or isopropanol. Accordingly, an "amphiphilic polymer coating" and "amphiphilic polymer or co-polymer" according to embodiments of the invention are dissolvable in both aqueous and non-aqueous solvents. It is to be appreciated that while all components included in the amphiphilic polymer coating may not necessarily be dissolvable in both aqueous and non-aqueous solvents, that the aggregate polymer matrix of the amphiphilic polymer coating is dissolvable in both aqueous and non-aqueous solvents. For example, embodiments of the invention may utilize water-soluble and/or water-insoluble therapeutic agents, as well as a water-insoluble wax, for example, interdispersed in the aggregate polymer matrix of the amphiphilic polymer coating. While an individual component or components of the amphiphilic polymer coating may not be dissolvable in both aqueous and non-aqueous solvents, the continuous aggregate polymer matrix may nevertheless be uniformly dissolved and removed from a substrate in both aqueous and non-aqueous solvents. Accordingly, the term amphiphilic polymer coating is understood to mean that the aggregate polymer matrix of the coating is uniformly dissolvable and removable from a substrate in both aqueous and non-aqueous solvents.

Amphiphilic Polymers or Co-polymers

In one aspect, embodiments of the invention disclose an amphiphilic polymer coating including one or more amphiphilic polymers or co-polymers. In an embodiment, the amphiphilic polymer or co-copolymer is a non-ionic thermoplastic polymer or co-polymer. For example, the amphiphilic polymer or co-copolymer can be hydroxypropyl cellulose (UPC). In an embodiment, the amphiphilic polymer or co-copolymer is complexed with iodine and the iodine is not covalently bonded to the amphiphilic polymer or co-copolymer. For example, polyvinyl pyrrolidone (PVP) and HPC may be complexed with iodine. PVP complexed with iodine is also known as povidone iodine. Surprisingly, as suggested by the results of Example 4, complexing a non-ionic amphiphilic polymer with iodine may increase solubility of paclitaxel in vivo and therefore assist in tissue uptake of paclitaxel. This can reduce the time requirements of the medical procedure and amount of mechanical pressure and/or metabolic insufficiencies caused by sustained inflation of the expandable structure. Complexing with iodine can also serve addition functions. It imparts an amber hue on the amphiphilic polymer coating, aiding in visualization outside of the body, and with the coating process. Additionally, as iodine has a large nuclear radius, it will provide radiopacity under fluoroscopy; the expandable structure will be visible under fluoro, and the dissolution of the amphiphilic polymer coating can be monitored as a function of time.

In an embodiment, the amphiphilic polymer or co-polymer is an ionic thermoplastic co-polymer or co-copolymer. For example, the amphiphilic polymer or co-copolymer can be poly (methyl vinyl ether-alt-maleic acid monobutyl ester) (available under the trade name Gantrez ES-425, from International Specialty Products (ISP), Wayne, N.J.) or poly (methyl vinyl ether-alt-maleic acid monoethyl ester) (available under the trade name Gantrez ES-225, from International Specialty Products (ISP), Wayne, N.J.).

UPC (non-iodinated), iodinated UPC, iodinated PVP (povidone iodine), poly (methyl vinyl ether-alt-maleic acid monobutyl ester), and poly (methyl vinyl ether-alt-maleic acid monoethyl ester) are soluble in lower alcohols without the use of any water, which provides for a low surface tension and rapid evaporation. They are also freely soluble in water resulting in rapid dissolution in vivo. In an embodiment, this is beneficial when it is desired that the therapeutic agent transfer take place within 90 to 300 seconds of inflation. When the above amphiphilic polymers or co-polymers are dissolved in sufficient ethanol, alone or in combination, they are also freely miscible with acetone. In an embodiment, where the therapeutic agent includes paclitaxel, this can be beneficial because paclitaxel is highly soluble in warm acetone, and the solvent combination enables a high drug loading. In another embodiment, the polymer or co-polymer may not be fully amphiphilic. For example, hydroxypropyl methyl cellulose is not fully soluble in non-aqueous solvent, however some grades are soluble in a solution which contains approximately 10% water and 90% non-aqueous solvent.

In an embodiment, the amphiphilic polymer coating may optionally include a plasticizer. A plasticizer may be particularly useful to increase the ductility and prevent the coating from cracking or delaminating while bending or folding in the dry state. Suitable plasticizers include, but are not limited to, polyethylene glycol with a molecular weight below 10 K Daltons, propylene glycol, triethyl citrate, glycerol, and dibutyl sebacate.

In an embodiment, the amphiphilic polymer coating may optionally include a wax. A wax-like surface assists with the gliding quality of the amphiphilic polymer coating in relation with a body lumen surface and/or in relation with an optional protective sheath over the amphiphilic polymer coating. Suitable waxes include, but are not limited to bees wax, carnauba wax, polypropylene glycol, polydimethyl siloxane (PDMS), and PDMS derivatives.

Therapeutic Agents

In another aspect, embodiments of the invention disclose an apparatus and method for delivering therapeutic agents to treat a variety of diseases that arise in body lumen walls. The therapeutic agents useful in accordance with the present invention may be used singly or in combination. The therapeutic agents may be non-aqueous soluble (i.e. solvent soluble) and/or aqueous soluble.

In an embodiment, non-aqueous soluble therapeutic agents are particularly useful as components in a coating composition which includes a majority or exclusively non-aqueous solvents. For example, a non-aqueous soluble anti-proliferative agent such as paclitaxel may be used in combination with another therapeutic agent such as the anti-inflammatory agent dexamethasone. In an embodiment, therapeutic agents which may be, singly or in combination, locally delivered to the surface of normal or diseased body lumens can be classified into the categories of anti-proliferative agents, anti-platelet agents, anti-inflammatory agents, anti-thrombotic agents, and thrombolytic agents. These classes can be further subdivided. For example, anti-proliferative agents can be anti-mitotic. Anti-mitotic agents inhibit or affect cell division, whereby processes normally involved in cell division do not take place. One sub-class of anti-mitotic agents includes vinca alkaloids. Representative examples of non-aqueous soluble vinca alkaloids include, but are not limited to, paclitaxel (including the alkaloid itself and naturally occurring forms and derivatives thereof, as well as synthetic and semi-synthetic forms thereof), vincristine, etoposide, indirubin, and anthracycline derivatives, such as, for example, daunorubicin, daunomycin, and plicamycin. Other sub-classes of anti-mitotic agents include anti-mitotic alkylating agents, such as, for example non-aqueous soluble fotemustine, and anti-mitotic metabolites, such as, for example, non-aqueous soluble azathioprine, mycophenolic acid, leflunomide, teriflunomide, fluorouracil, and cytarabine. Anti-mitotic alkylating agents affect cell division by covalently modifying DNA, RNA, or proteins, thereby inhibiting DNA replication, RNA transcription, RNA translation, protein synthesis, or combinations of the foregoing.

Examples of non-aqueous soluble anti-inflammatory agents that can also be used include, but are not limited to, dexamethasone, prednisone, hydrocortisone, estradiol, triamcinolone, mometasone, fluticasone, clobetasol, and non-steroidal anti-inflammatories, such as, for example, acetaminophen, ibuprofen, and sulindac. The arachidonate metabolite prostacyclin or prostacyclin analogs are examples of a vasoactive antiproliferative.

Therapeutic agents with pleiotropic effects on cell proliferation, immunomodulation and inflammation may also be used. Examples of such non-aqueous soluble agents include, but are not limited to the macrolides and derivatives thereof such as sirolimus, tacrolimus, everolimus, temsirolimus.

Anti-platelet agents are therapeutic entities that act by (1) inhibiting adhesion of platelets to a surface, typically a thrombogenic surface, (2) inhibiting aggregation of platelets, (3) inhibiting activation of platelets, or (4) combinations of the foregoing. Non-aqueous soluble anti-platelet agents that act as inhibitors of adhesion of platelets include, but are not limited to, and tirofiban and RGD (Arg-Gly-Asp)-based peptides (Pegylated) that inhibit binding to gpIIbIIIa or .alpha.v-.beta.3, compounds that block P-selectin or E-selectin binding to their respective ligands. Agents that inhibit ADP-mediated platelet aggregation include, but are not limited to, cilostazol.

Anti-thrombotic agents include chemical and biological entities that can intervene at any stage in the coagulation pathway. Examples of specific non-aqueous soluble entities include, but are not limited to, small molecules that inhibit the activity of factor Xa. Also included are direct thrombin inhibitors, such as, for example, argatroban, inogatran.

Other non-aqueous soluble therapeutic agents that can be used are cytotoxic drugs, such as, for example, apoptosis inducers, and topoisomerase inhibitors, including, irinotecan, and doxorubicin, and drugs that modulate cell differentiation such as inhibitors of histone deacetylase, including valproic acid.

Other non-aqueous soluble therapeutic agents that can be used include anti-lipaedemic agents, including but not limited to fenofibrate, clofibrate, and rosiglitazone and matrix metalloproteinase inhibitors, such as, for example, batimistat, antagonists of the endothelin-A receptor, such as, for example, darusentan.

In another embodiment, aqueous soluble therapeutic agents may be used. Aqueous soluble anti-mitotic agents include Epothilone A, Epothilone B and Epothilone D, and all other Epothilones. Aqueous soluble anti-platelet agents include RGD (Arg-Gly-Asp)-based peptides that inhibit binding to gpIIbIIIa or .alpha.v.beta.3. Aqueous soluble anti-thrombotic agents include heparinoid-type agents that can inhibit both FXa and thrombin, either directly or indirectly, such as, for example, heparin, heparin sulfate, low molecular weight heparins, such as, for example, the compound having the trademark Clivarin.R™, and synthetic oligosaccharides, such as, for example, the compound having the trademark Arixtra.R™. Aqueous soluble thrombolytic agents, which may be defined as agents that help degrade thrombi (clots), can also be used as adjunctive agents, because the action of lysing a clot helps to disperse platelets trapped within the fibrin matrix of a thrombus. Representative examples of thrombolytic agents include, but are not limited to, urokinase or recombinant urokinase, pro-urokinase or recombinant pro-urokinase, tissue plasminogen activator or its recombinant form, and streptokinase. Additional aqueous soluble therapeutic agents include recombinant antibodies for anti-platelet and anti-endothelin applications.

When used in the above or other treatments, a therapeutically effective amount of one of the non-aqueous soluble or aqueous soluble therapeutic agents in embodiments of the invention may be employed in pure form or, where such forms exist, in pharmaceutically acceptable salt, ester or prodrug form. Alternatively, the therapeutic agent may be administered as a pharmaceutical composition including the compound of interest in combination with one or more pharmaceutically acceptable excipients. As used herein, the phrase "therapeutically effective amount" of the therapeutic agents of the invention means a sufficient amount of the therapeutic agents to treat disorders, at a reasonable benefit/risk ratio applicable to any medical treatment. It will be understood, however, that the total daily usage of the therapeutic agents and compositions of embodiments of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the therapeutic agent at levels lower than required to achieve the desired therapeutic effect and to gradually increase the dosage until the desired effect is achieved.

Coating Process

Figure 1B:
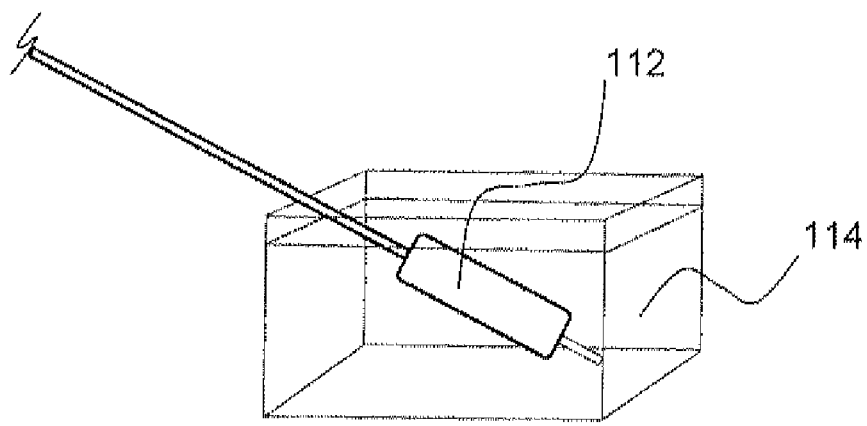
FIG. 1B is an isometric view illustration of a balloon catheter dipped in a coating solution while the balloon is in the expanded position.
Figure 1C:
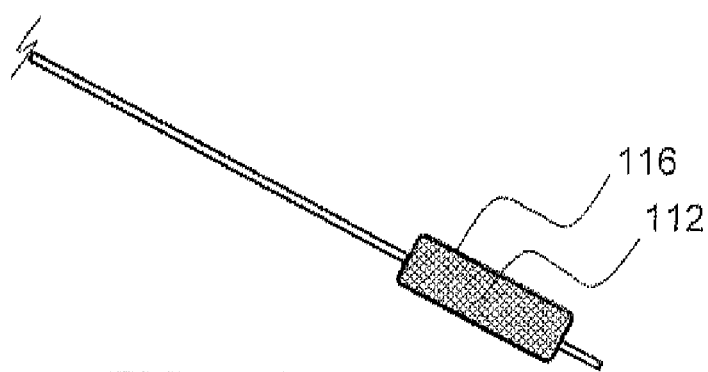
FIG. 1C is a side view illustration of a balloon catheter with a coated balloon surface.

The amphiphilic polymer coating containing a therapeutic agent or agents and an amphiphilic polymer or co-polymer can be formed from with a variety of techniques including deposition, spray coating, and dip coating. FIG. 1A-FIG. 1C are illustrations of a particular embodiment in which the amphiphilic polymer coating is formed by dip coating the expandable structure of a medical disposable device, such as the balloon of a balloon catheter, into a coating solution or coating mixture. Utilizing embodiments of the invention, the dip coating process can provide a uniform therapeutic agent density across the balloon surface using a simple and reproducible single-dip, thereby eliminating the need for multiple dips to load the therapeutic agent into the coating.

FIG. 1A is an illustration of a balloon catheter 110 with an uncoated balloon 112 in the expanded position (e.g. inflated). As shown in FIG. 1B, the uncoated expanded balloon 112 can be dipped into a coating solution or mixture 114. As described above, the coating solution 114 may include aqueous or more preferably non-aqueous solvents, an amphiphilic polymer or co-polymer, and a therapeutic agent. The coating solution 114 may optionally include additional components such as a plasticizer and/or wax. In an embodiment, the coating solution 114 viscosity is at least 5 cps and less than approximately 75 cps. After dipping the expanded balloon 112 into the coating solution 114, the expanded balloon 112 is then removed from the coating solution, as shown in FIG. 1C resulting in a uniform coating 116 on the expanded balloon 112. In an embodiment, optionally a gas (e.g. argon, oxygen) plasma may be used on the catheter prior to coating to enhance the coating adhesion.

In an embodiment, the use of an amphiphilic polymer or co-polymer and non-aqueous soluble therapeutic agent enables the use of non-aqueous solvents to dissolve the polymer or co-polymer and therapeutic agent. A majority or exclusively non-aqueous solvents in the coating solution provides rapid evaporation, a lower surface tension, and improved substrate wetting compared to an aqueous solution, which aids in obtaining coating uniformity. For example, solvents with boiling points lower than water can be used singly or in combination in the coating solution 114, such as ethanol, methanol, or methyl ethyl ketone, isopropanol (2-propanol), and/or butanol that rapidly evaporate in ambient conditions, which consequently reduces gravity induced surface defects such as sagging. Dip coating into a coating solution with majority or exclusively non-aqueous solvents permits forming a coating with high levels of a therapeutic agent, and permits forming a coating that provides a uniform therapeutic agent density across the balloon surface using a simple, reproducible and hence easily manufacturable application process. For example, when HPC (non-iodinated), iodinated UPC, iodinated PVP (povidone iodine), poly (methyl vinyl ether-alt-maleic acid monobutyl ester), and poly (methyl vinyl ether-alt-maleic acid monoethyl ester) are dissolved in sufficient ethanol, they are also freely miscible with acetone. In an embodiment, where the therapeutic agent includes paclitaxel, this can be beneficial because paclitaxel is highly soluble in warm acetone, and the solvent combination enables a high drug loading. After coating, the balloon is dried, deflated and folded for delivery.

In an embodiment, after the balloon is dried, but before deflating and folding for delivery, the balloon may optionally be dip coated into a separate coating solution containing a wax to form a thin wax coating (not shown) over the amphiphilic polymer coating, rather than incorporating the wax into the amphiphilic polymer coating.

In alternate embodiments, where the therapeutic agent is not soluble in non-aqueous solutions, an aqueous solution may be used.

Local Therapeutic Agent Delivery Process

Figure 2A:
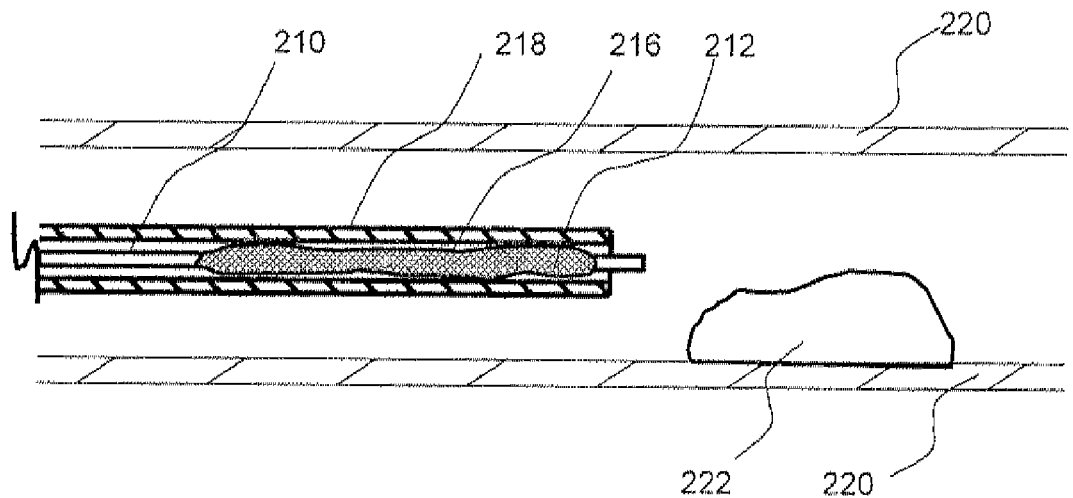
FIG. 2A is a side view illustration of an amphiphilic polymer coating disposed on an outer surface of unexpanded balloon of a balloon catheter covered by a retractable sheath and inserted into a body lumen.
Figure 2B:
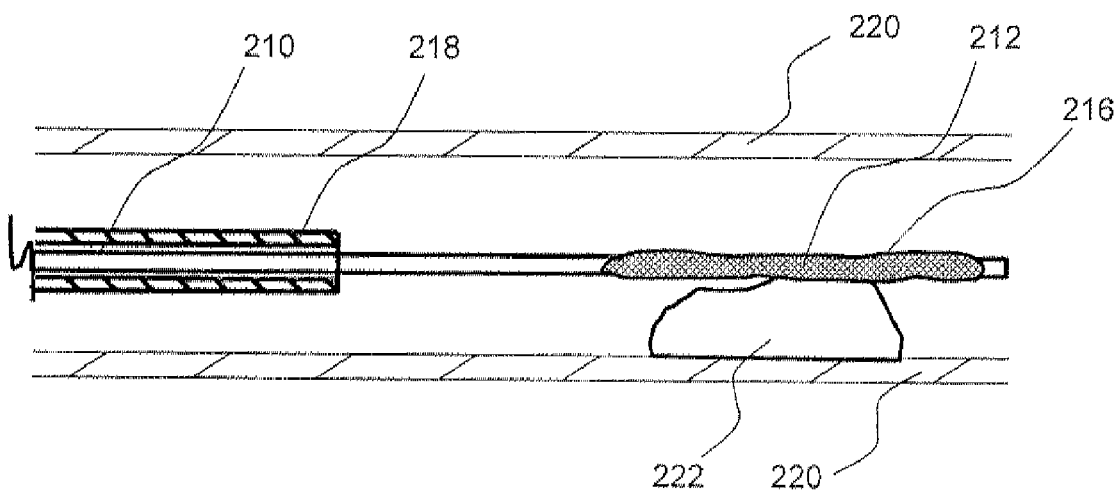
FIG. 2B is a side view illustration of an amphiphilic polymer coating disposed on an outer surface of unexpanded balloon of a balloon catheter adjacent to the focal area of local therapeutic agent delivery within a body lumen.
Figure 2C:
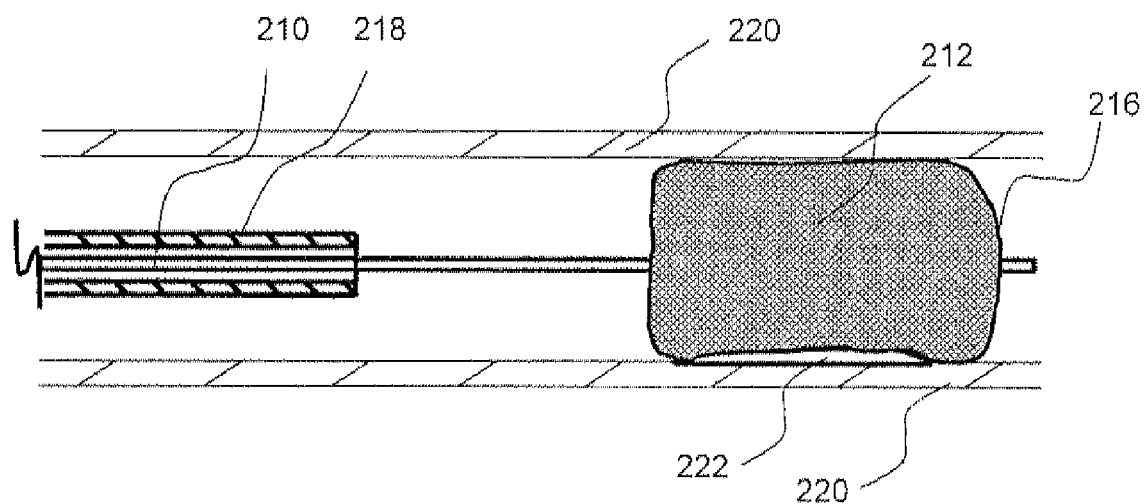
FIG. 2C is a side view illustration of the interface of the amphiphilic polymer coating disposed on an outer surface of an expanded balloon of a balloon catheter and the focal area of local therapeutic agent delivery within a body lumen.

FIG. 2A-FIG. 2C are illustrations of a particular embodiment in which the amphiphilic polymer coating comprising a therapeutic agent and amphiphilic polymer or co-polymer is locally delivered to the surface of a body lumen. As shown in FIG. 2A a balloon catheter 210 having an amphiphilic polymer coating 216 disposed on an unexpanded balloon 212 is provided and inserted into a body lumen 220. The catheter 210 may additionally include an optional protective sheath 218 over the unexpanded balloon 212 to prevent the amphiphilic polymer coating 216 from prematurely dissolving when the catheter is inserted into the body lumen 220. In an embodiment, the body lumen 220 may be an artery including a focal area 222, such as an unperturbed primary atheroscolerotic or restenotic lesion. In an embodiment, the body lumen 220 may be a common bile duct or a branch of a common bile duct and focal area 222 is an intraluminal tumor.

As shown in FIG. 2B, the unexpanded balloon 212 is positioned adjacent the focal area 222 and the protective sheath 218 is retracted. The balloon 212 is then expanded (by inflation or otherwise) to contact the amphiphilic polymer coating 216 on the expanded balloon 212 against the body lumen 220 where the focal area 222 exists. In an embodiment, the expanded balloon 212 is a balloon catheter and the balloon is expanded to 2-20 atmospheres. Being amphiphilic, the coating 216 dissolves immediately when exposed to aqueous fluids such as blood in vivo. In an embodiment, at least 90% of the amphiphilic polymer coating 216 is dissolved within 300 seconds of inflating. In an embodiment, at least 90% of the amphiphilic polymer coating 216 is dissolved within 90 seconds of inflating.

In clinical use for angioplasty, it may be preferable for the balloon 212 to be expanded for only 5 to 300 seconds. This time limitation is a due to the type of medical procedure because a longer use time with the balloon inflated could result in the focal or adjacent tissue damage that is deleterious to the therapeutic intent of the procedure. This damage could result from mechanical pressure and/or metabolic insufficiency caused by sustained inflation of the balloon including but not limited to tissue architecture, tissue inflammation, cell death, and induction of reactive scarring within the organ. In an embodiment, a coated angioplasty balloon may be tracked to a target lesion using standard techniques, the optional protective sheath is retracted and the angioplasty balloon is inflated against an artery wall. Hydration of the coating occurs immediately and causes the therapeutic agent to release into tissue, the coating polymer or co-polymer to dissolve, and some of the amphiphilic polymer coating to transfer from the balloon to the artery wall. This paving acts as drug reservoir and is transient. The total solubility of the polymer or co-polymer in blood prevents any embolic hazard associated with the coating. Also, this active dissolution of the polymer or co-polymer matrix assists the transfer of hydrophobic therapeutic agents such as paclitaxel from the balloon to the tissue.

Several embodiments of the invention are described below with reference to the following non-limiting Examples regarding coating of PET coupons. Solution percentages provided are by weight.

EXAMPLE 1

One (1.0) grams of a 7.5% solution of 60 K Dalton UPC in ethanol is mixed with 0.15 grams of 1% solution of propylene glycol (plasticizer) in acetone, 0.075 grams paclitaxel and 0.08 grams n-butanol. The mixture is heated in a water bath to dissolve the paclitaxel; a clear solution results. When dip coated (single dip) on PET coupons at a dip speed of about 10 inches/minute, and dried at room temperature, there results a slightly milky dry coating. About 3 cm$^2$ of coupon surface is coated per coupon. The average coating density determined by gravimetric analysis is 6 ug/mm$^2$ and the implied paclitaxel density is 3 ug/mm². The dry coating is sufficiently ductile to withstand a 180 degree bend without cracking or delaminating.

A coupon coated as above is immersed in 3 ml of 37° C. water for 3 minutes with agitation, after which the coupon is removed and the turbid suspension diluted with 9 ml dimethyl sulfoxide (DMSO) to produce a clear solution. Quantitative UV analysis at 260 nm and 280 nm vs. a standard curve shows an 88% recovery. This result demonstrates the rapid dissolution of the amphiphilic polymer coating and drug release in vitro. The in vivo milieu is expected to present serum proteins with a surfactant effect, which will increase the dissolution rate of the drug and coating polymer in vivo.

EXAMPLE 2

0.075 grams paclitaxel is mixed with 0.9 grams of a 20% povidone-iodine solution in 2-propanol, 0.06 grams of a 10% propylene glycol solution in 2-propanol and 0.04 grams acetone. When dip coated (single dip) on a PET coupon at a dip speed of 10 inches /min, and dried at room temperature, there results a clear amber dry coating. About 2.5 ug/mm² of paclitaxel is deposited.

The above coupon is immersed in 1.5 ml of 37° C. water for 30 seconds. All of the coating dissolves in the water, and the solution is totally transparent amber, and not turbid as in Example 1.

EXAMPLE 3

An identical formula to Example 2 is made, however non-iodinated PVP is employed instead of povidone-iodine of the same molecular weight (40 K Dalton). When dip coated (single dip) on a PET coupon at a dip speed of 10 inches /min, and dried at room temperature, there results a clear water white dry coating. About 2.5 ug/mm² of paclitaxel is deposited.

This coupon is immersed in 1.5 ml of 37° C. water for 30 seconds. All of the coating polymer dissolves in the water, and the solution shows a suspension of needle crystals. This suspension becomes more turbid after 24 hours, while the above amber solution from Example 2 remains transparent. This demonstrates that the povidone-iodine changes the aqueous solubility of paclitaxel.

EXAMPLE 4

Light scattering experiments at 600 nm and 700 nm were performed comparing the drug (paclitaxel) and polymer eluted water solutions of Example 2 (containing povidone-iodine) with Example 3 (containing non-iodinated PVP). The results shown in Table I below provide a quite unexpected three-fold increase in solubility of paclitaxel in the povidone-iodine eluted water solution of Example 2 compared to the non-iodinated PVP eluted water solution of Example 3. Consequently, and quite unexpectedly this suggests that the iodine complexed povidone-iodine polymer may assist in tissue uptake of the therapeutic agent paclitaxel in vivo.

TABLE I

| Optical density measurements | | |
| --- | --- | --- |
| Wavelength | Polymer | Optical Density |
| 600 nm | PVP-iodinated | 0.120 |
| 600 nm | PVP (non-iodinated) | 0.359 |
| 700 nm | PVP-iodinated | 0.089 |
| 700 nm | PVP (non-iodinated) | 0.284 |

Diseases of the Vasculature

One therapeutic area where embodiments of the present invention will be applicable is the treatment of luminal disorders of the vasculature. In general, luminal disorders may be classified as native (atherosclerotic, thromboembolic) or iatrogenic (restenosis) diseases. These luminal disorders may include but not be limited to atherosclerosis, atheromatous lesions, vulnerable plaque, thromboembolic obstructions, vascular graft disease, arteriovenous fistula disease, arteriovenous graft disease and restenosis.

Atherosclerosis is a complex disease of the vessel wall involving the interplay of inflammation, proliferation, lipid deposition and thrombus formation. Atherosclerosis promotes the formation of atheromatous plaques that may progress slowly over several years, leading to progressive obstruction of the vessel lumen manifesting clinically as angina. Atheromatous plaques, may also become "vulnerable plaques" due to an unstable collection of white blood cells (primarily macrophages) and lipids (including cholesterol) in the wall of an artery and become particularly prone to rupture. A rupture of a vulnerable plaque is commonly believed to be the cause of sudden thrombotic obstructions of the vessel lumen due to the rapid formation of blood clots at the rupture site, leading to the clinical manifestations of heart attack or stroke. Vulnerable plaques may not significantly obstruct a vessel lumen until rupture, thus they are pre-obstructive lesions. It is envisioned that a desirable therapeutic target is the prevention of obstruction of the vessel lumen by the treatment of vulnerable plaques prior to their rupture. Specifically, embodiments of the present invention could be applied to a catheter with a tip that is expandable to allow uniform and complete contact with and delivery of therapeutic agents to sites of luminal atheromatous or vulnerable plaques. The local delivery of therapeutic agents would enable a much higher, targeted, local concentration of said agents than might otherwise be achieved by systemic delivery. Moreover, a local delivery strategy would enable the use of therapeutic agents that otherwise may be poor candidates for systemic delivery due to lack of bioavailability and/or undesirable or toxic side effects at concentrations needed to achieve efficacy.

Restenosis

One therapeutic area where embodiments of the present invention will be applicable is inhibiting the process of restenosis. Restenosis is the result of a complex process involving inflammation and proliferation activated by a response to a percutaneous or surgical vascular intervention. Examples of these percutaneous or surgical interventions may include but are not limited to the revascularization of vascular bypass grafts, arteriovenous fistulas, arteriovenous grafts and percutaneous revascularization of coronary, femoral, and carotid vessels. Atherosclerotic plaque arising from the arterial wall can reduce cross-sectional flow area which limits flow to downstream organs. Cross-sectional flow area can be restored by displacing (e.g. expandable balloon or stent) or removing the lesion (e.g. directional or rotational atherectomy). In the months to weeks after revascularization local proliferative of arterial wall smooth muscle cells can create an obstruction to flow at the site of the original atherosclerotic plaque. Paclitaxel is a diterpene molecule containing a complex taxane ring that inhibits cytokinesis by promoting microtubule polymerization. Paclitaxel inhibits smooth muscle cell proliferation and restenosis after balloon angioplasty in a mammalian arteries. Paclitaxel inhibits restenosis after percutaneous coronary revascularization in humans when it is delivered over days to weeks from implanted metal stents that were retained after the revascularization procedure. Brief exposure to paclitaxel (20 minutes of less) can inhibit smooth muscle cell proliferation for sustained periods (14 days). Clinical studies demonstrate that paclitaxel can also effectively inhibit restenosis after femoral and coronary revascularization when it is delivered over a short period (minutes) from an expandable balloon coated with the drug.

Restenosis is a complex molecular process that involves both smooth muscle cell proliferation in addition to inflammatory processes. Dexamethasone is a glucocorticoid that reduces inflammation and restenosis after balloon angioplasty in a mammalian arteries. This suggests that there may be clinical benefit in delivering antimitotic agents such as paclitaxel in combination with anti-inflammatory agents such as dexamethasone from an expandable balloon coated with the two therapeutic agents.

Pulmonary Disease

Another therapeutic area where embodiments of the present invention could be applicable is a luminal surface of normal or diseased airway for the treatment or prevention of focal diseases of the lung and airways. This embodiment may be used in conjunction with both a rigid or flexible bronchoscope which are commonly used to facilitate access to and visualization of the target treatment area.

In general, focal diseases of the airways area neoplasms that are categorized as either benign or malignant. Primary neoplasms may be classified as epithelial, mesenchymal or lymphoid tumors; more than 20 types of tracheal neoplasms have been described.

Carcinoid tumors represent approximately 85 percent of adenomas of the tracheobronchial tree. Adenoid cystic carcinoma is the most frequent adenoma of the trachea. Adenoid cystic carcinoma (or cylindroma) is the second most common malignancy and also the second most common primary tracheal neoplasm.

Conventional treatment for lung cancer can involve surgical removal of tumor, chemotherapy, or radiation therapy, as well as combinations of these methods. The decision about which treatments will be appropriate take into account the localization and extent of the tumor as well as the overall health status of the patient. An example of adjuvant therapy is chemotherapy or radiotherapy administered after surgical removal of a tumor in order to be certain that all tumor cells are killed.

Depending upon the specific neoplasm type and behavior as well as the time of diagnosis, the neoplasm may or may not present a physical obstruction or protrusion into the lumen of the airways. It is envisioned that an approach to restoring functional luminal patency could be to mechanically restore luminal patency by displacing the tumor with a balloon or reduce tumor bulk and then locally delivering a drug to inhibit tumor growth and/or tumor survival. Local drug delivery using embodiments of the present invention could be an effective method of delivering chemotherapeutic agents effective against benign or malignant neoplasms to the luminal aspect of the tumor. Specifically, embodiments of the present invention could be applied to a catheter or a bronchoscope and advanced antegradely or retrogradely to the intended site of local drug delivery. It is envisioned that embodiments of the present invention will enable the local delivery of bioactive (therapeutic) agents to the surface of normal or diseased airway lumens and may be used singly or in combination with surgical removal, chemotherapy and radiation therapy. The local delivery of therapeutic agents would enable a much higher, targeted, local concentration of said agents than might otherwise be achieved by systemic delivery. Moreover, a local delivery strategy would enable the use of therapeutic agents that otherwise may be poor candidates for systemic delivery due to lack of bioavailability and/or undesirable or toxic side effects at concentrations needed to achieve efficacy. The targeted local delivery of therapeutic agents may be used to reduce tumor size to facilitate surgical removal and may eliminate the need for and/or reduce the duration or intensity of systemic chemotherapy or radiotherapy which have numerous unpleasant side effects.

Gastrointestinal Disease

Another therapeutic area where embodiments of the present invention could be applicable is gastrointestinal disease including, but limited to, benign and malignant tumors of the esophagus, biliary tract, colon, and small bowel.

Esophageal tumors are caused by dysregulated division of esophageal smooth muscle or epithelial cells. The tumors can be either benign (e.g. leiomyoma) or malignant (squamous cell carcinoma or adenocarcinoma). These tumors can grow into the lumen and compromise the functional cross-sectional area of the esophagus causing dysphagia (abnormal swallowing) and consequent malnutrition.

It is envisioned that an approach to restoring functional luminal patency could be to mechanically restore luminal patency by displacing the tumor with a balloon or metal dilator or reduce tumor bulk (e.g. laser ablation), and then locally delivering a therapeutic agent to inhibit tumor growth and/or tumor survival. Local therapeutic agent delivery using embodiments of the present invention could be an effective method of delivering chemotherapeutic agents effective against benign or malignant esophageal tumors to the luminal aspect of the tumor. Specifically, embodiments of the present invention could be applied to a catheter or an endoscope and advanced antegradely or retrogradely to the intended site of local drug delivery. Chemotherapeutic agents that could be effective in this manner include, but are not limited to, microtubule stabilizing agents (e.g. taxanes including paclitaxel and epothilones), topoisomerase I inhibitors (e.g. irinotecan), platinum derivatives (e.g. oxaliplatin, cisplatin, carboplatin), anthracyclines (daunorubicin, epirubicin), 5-FU, and targeted biologic therapies (e.g. anti-VEGF antibodies such as bevacizumab). The advantages of this method are that high doses of effective chemotherapeutic agents can be delivered to the tumor without systemic toxicity, the patient's diet would not have to be modified to prevent food impaction, and the mechanical complications of stent placement including indirect tracheal compression, stent migration, and stent occlusion could be avoided. Therapeutic agent for the above indication that exhibit water-only solubility or require water for solubilization such as carboplatin, cisplatin, the epothilones, and targeted proteins such as antibodies (such as the anti-VEGF antibody bevacizumab) can be formulated into the disclosed amphiphilic polymer coating by the use of water as part or all of the solvent.

A similar approach could be used with malignancies of the biliary tract. Cholangiocarcinoma is the most common biliary tract malignancy. It is caused by dysregulated division of cholangiocytes. These tumors can compromise the functional lumen of the intra- or extra-hepatic biliary tree causing cholestasis and consequent cholangitis, pruritis, fat malabsorption, and anorexia.

It is envisioned that an approach to restoring functional luminal patency could be to mechanically restore luminal patency by displacing the tumor with a balloon, blade, or metal dilator or reduce tumor bulk (e.g. laser ablation), and then locally deliver a therapeutic agent to inhibit tumor growth and/or tumor survival utilizing embodiment of the present invention. Chemotherapeutic agents that could be effective in this manner include, but are not limited to, microtubule stabilizing agents (e.g. taxanes including paclitaxel and epothilones), platinum derivatives (e.g. oxaliplatin, cisplatin, carboplatin), anthracyclines (daunorubicin, epirubicin), 5-FU, DNA cross-linkers (mitomycin-C), alkylating nitrosoureas (lomustine), interferons (interferon-alpha), and targeted biologically active agents (e.g. EGFR inhibitors such as cetuximax). The advantages of this method are that high doses of effective chemotherapeutic agents can be delivered to the tumor without systemic toxicity, and the mechanical complications of stent placement including stent migration and stent occlusion could be avoided.

Approaches similar to that described above for esophageal and biliary tract malignancies could be developed for small bowel and colonic malignancies. Analogous approaches could also be used to locally delivery therapeutic agents to non-malignant gastrointestinal diseases (e.g. anti-inflammatory agents delivered to treat inflammatory bowel disease). Therapeutic agents for the above indication that exhibit water-only solubility or require water for solubilization such as carboplatin, cisplatin, the epothilones, interferons (interferon-alpha) and targeted proteins such as antibodies (such as the EGFR inhibitor cetuximab) can be formulated into the disclosed amphiphilic polymer coating by the use of water as part or all of the solvent system.

In the foregoing specification, various embodiments of the invention have been described. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A medical disposable device comprising:
an expandable structure having an outer surface; and
an amphiphilic polymer coating disposed on the outer surface of the expandable structure, said amphiphilic polymer coating comprising an amphiphilic polymer or co-polymer complexed with iodine and a hydrophobic therapeutic agent interdispersed in said amphiphilic polymer or co-polymer complexed with iodine;
wherein at least 90% of said amphiphilic polymer coating is dissolved within 300 seconds of expanding said expandable structure in vivo.

2. The medical disposable device of claim 1, wherein said amphiphilic polymer or co-polymer is a non-ionizable thermoplastic.

3. The medical disposable device of claim 2, wherein said amphiphilic polymer or co-polymer is selected from the group consisting of hydroxypropyl cellulose (HPC) and polyvinyl pyrrolidone (PVP).

4. The medical disposable device of claim 2, wherein said amphiphilic polymer coating further comprises a plasticizer selected from the group consisting of polyethylene glycol with a molecular weight below 10 K Daltons, propylene glycol, triethyl citrate, glycerol, and dibutyl sebacate.

5. The medical disposable device of claim 2, wherein said amphiphilic polymer coating further comprises a wax selected from the group consisting of bees wax, carnauba wax, polypropylene glycol, polydimethyl siloxane (PDMS), and PDMS derivatives.

6. The medical disposable device of claim 2, wherein said hydrophobic therapeutic agent is selected from the group consisting of an anti-proliferative agent, anti-platelet agent, anti-inflammatory agent, anti-thrombotic agent, and thrombolytic agent.

7. The medical disposable device of claim 2, wherein said hydrophobic therapeutic agent is selected from the group consisting of paclitaxel and dexamethasone acetate.

8. The medical disposable device of claim 2, further comprising a sheath which is extendable over and retractable from said expandable structure.

9. The medical disposable device of claim 2, wherein said expandable structure is a balloon of a balloon catheter.

10. A medical disposable device comprising:
an expandable structure having an outer surface; and
a coating disposed on the outer surface of the expandable structure, said coating consisting essentially of at least one amphiphilic polymer or co-polymer complexed with iodine and at least one hydrophobic therapeutic agent interdispersed in said at least one amphiphilic polymer or co-polymer complexed with iodine;
wherein at least 90% of said coating is dissolved within 300 seconds of expanding said expandable structure in vivo.

11. The medical disposable device of claim 10, wherein said hydrophobic therapeutic agent is selected from the group consisting of an anti-proliferative agent, anti-platelet agent, anti-inflammatory agent, anti-thrombotic agent, and thrombolytic agent.

12. The medical disposable device of claim 10, wherein said coating further comprises a plasticizer at a concentration of less than 20% wt of said at least one amphiphilic polymer or co-polymer complexed with iodine.

13. The medical disposable device of claim 10, wherein said coating further comprises a wax at a concentration of less than 1% wt of said at least one amphiphilic polymer or co-polymer complexed with iodine.

14. The medical disposable device of claim 10, wherein said expandable structure is a balloon of a balloon catheter.

15. A medical disposable device comprising:
an expandable structure having an outer surface; and
a coating layer disposed on the outer surface of the expandable structure, the coating layer comprising non-covalently bound iodine and a hydrophobic therapeutic agent interdispersed throughout an aggregate polymer matrix of the coating layer;
wherein the aggregate polymer matrix is dissolvable in both aqueous and non-aqueous solvents.

16. The medical disposable device of claim 15, wherein the hydrophobic therapeutic agent is selected from the group consisting of an anti-proliferative agent, anti-platelet agent, anti-inflammatory agent, anti-thrombotic agent, and thrombolytic agent.

17. The medical disposable device of claim 15, wherein the hydrophobic therapeutic agent is selected from the group consisting of paclitaxel and dexamethasone acetate.

18. The medical disposable device of claim 15, further comprising a sheath which is extendable over and retractable from the expandable structure.

19. The medical disposable device of claim 15, wherein the expandable structure is a balloon of a balloon catheter.

20. The medical disposable device of claim 15, wherein the coating layer further comprises a plasticizer.

21. The medical disposable device of claim 15, wherein the coating layer further comprises a wax.

* * * * *